United States Patent [19]
Evans et al.

[11] Patent Number: 5,792,147
[45] Date of Patent: Aug. 11, 1998

[54] VIDEO-BASED SYSTEMS FOR COMPUTER ASSISTED SURGERY AND LOCALISATION

[75] Inventors: Richard John Evans, Winchester; Christopher George Harris, West Wellow; Alan Charles Francis Colchester, Stowting, all of England

[73] Assignees: Roke Manor Research Ltd., Romsey; United Medical & Dental School, London, both of England

[21] Appl. No.: 897,670

[22] Filed: Jul. 21, 1997

Related U.S. Application Data

[63] Continuation of Ser. No. 404,825, Mar. 14, 1995, abandoned.

[30] Foreign Application Priority Data

Mar. 17, 1994 [GB] United Kingdom ............ 9405299

[51] Int. Cl.$^6$ .......................................... A61B 19/00
[52] U.S. Cl. .................................................. 606/130
[58] Field of Search .......................... 606/130, 129; 378/901

[56] References Cited

U.S. PATENT DOCUMENTS

| 4,831,645 | 5/1989 | Guenther et al. | 378/205 |
|---|---|---|---|
| 4,941,164 | 7/1990 | Schuller et al. | 378/205 |
| 4,991,579 | 2/1991 | Allen | 606/130 |
| 5,098,426 | 3/1992 | Sklar et al. | 606/5 |
| 5,129,911 | 7/1992 | Siczek et al. | 606/130 |
| 5,247,555 | 9/1993 | Moore et al. | 378/4 |
| 5,389,101 | 2/1995 | Heilbrun et al. | 606/130 |
| 5,398,684 | 3/1995 | Hardy | 128/653.1 |
| 5,414,459 | 5/1995 | Bullwinkel | 348/53 |
| 5,446,548 | 8/1995 | Gerig et al. | 356/375 |
| 5,517,990 | 5/1996 | Kalfas et al. | 606/130 |
| 5,526,812 | 6/1996 | Dumoulin et al. | 606/130 |

FOREIGN PATENT DOCUMENTS

| 0429148 | 5/1991 | European Pat. Off. |
| 2 246 261 | 5/1994 | United Kingdom . |
| 90/05494 | 5/1990 | WIPO . |

OTHER PUBLICATIONS

"A Computer-Assisted System for 3-D Frameless Localization in Stereotaxic MRI," by Patrick Clarysse et al., IEEE Transactions on Medical Imaging, vol. 10, No. 4, Dec. 1991, pp. 523–529.

"Vislan," A Technical Summary for Surgeons and Radiologists, prepared by Richard Evans, et al., Roke Manor Research, Nov. 1995.

Harris, C.G., et al., "Geometric Camera Calibration for Vision–Based Navigation", *Proceedings of IFAC International Workshop on Autonomous Vehicles*, 18–21 Apr. 1993, Southhampton, UK, pp. 77–82.

Colchester, A.C.F., et al., "Vislan: Combining Intra–Operative Video and Pre–Operative Images for Surgical Guidance", *Proc Applications of Computer Vision in Medical Image Processing*, Ed: GM Wells III, Menlo Park: AAAI Press, 1994, pp. 52–55.

Thomas, D.G.T., et al., "Minimally Invasive Surgery—Neurosurgery", *BMJ*, vol. 308, 8 Jan. 1994, pp. 126–128.

Hill, Derek L.G., et al., "Medical Image Registration Using Knowledge of Adjacency of Anatomical Structures", *Image and Vision Computing*, vol. 12, No. 3, 3 Apr. 1994 pp. 173–178.

*Primary Examiner*—Robert A. Hafer
*Assistant Examiner*—Justine R. Yu
*Attorney, Agent, or Firm*—Evenson, McKeown, Edwards & Lenahan, PLLC

[57] ABSTRACT

The apparatus comprises video cameras for viewing part of a patient's body and a slide projector for projecting a predetermined pattern of light onto the patient's body which is viewed by the cameras. A workstation and video frame grabber performs controlling and processing functions and are arranged to process said images from the cameras using image processing algorithms. The images from the cameras are superimposed upon prestored images which are generated from X-ray or CT scans. A passive pointer, having a predetermined pattern thereon which is recognisable by the controlling and processing means is used by the surgeon. The pattern is used to identify the exact position of a tip of the pointer in relation to the patient's body and is displayed on a monitor with the superimposed images.

17 Claims, 4 Drawing Sheets

VIDEO-BASED SYSTEMS FOR COMPUTER ASSISTED SURGERY AND LOCALISATION

This is a continuation of application Ser. No. 08/404,825, filed Mar. 14, 1995, abandoned.

BACKGROUND OF THE INVENTION

1. Field of the Invention

This invention concerns assistance to a surgeon performing an operation who has planned his work from images obtained from pre-operative medical imagers such as X-ray Computer Tomography (CT) or Magnetic Resonance (MR) Imagers. The invention's main concern is neurosurgery though other applications are possible. At the time of surgery, the surgeon would benefit from a means of relating visually detectable patient features to the pre-operatively generated images and plans. This process is known as localisation.

2. Description of Related Art

A number of partially successful localisation methods have been developed. One set of methods is known as frame-based stereotaxy [reviewed by D G T Thomas, N D Kitchen: "Minimally Invasive Surgery—Neurosurgery" British Medical Journal Vol 308, 8 Jan. 1994]. In these methods a frame is attached rigidly to the patient, by screws into the skull, before pre-operative imaging and remains in place in surgery. The design of the frame is such that it is visible in the pre-operative imagery and the surgery is planned in terms of measurements relative to the frame, so that the plan can be carried out by means of scales and graduations marked on the frame and visible to the surgeon in-theatre. This approach has the following disadvantages:

The need for surgery may not have been determined at the time of imaging so a frame may not have been in place, in which case second scan would be required.

The frame is painful for the patient and there are infection risks due to the invasive form of attachment. (Some forms of frame have been developed where part of the frame is detachable, which makes it slightly more comfortable but the infection risks are unchanged. Other forms of frame use bite-blocks (which fix via mouldings of the patient's teeth); these are less accurate because of the lack of rigidity in the fixing).

The frame itself can obstruct the surgeon's access, limiting the type of surgery which can be performed.

The other set of methods are known as frame-less or open-stereotaxy. Here, localisation is achieved using a patient feature (which is visible in pre-operative imagery) or a set of features and a corresponding feature or features locatable intra-operatively (i.e. in-theatre). These features provide a common reference for surgical planning and implementation of the plan in-theatre [see Thomas and Kitchen above]. These methods generally achieve localisation in the following way:

The patient's head is clamped using a device such as a Mayfield clamp, to keep it stationary. [The Mayfield clamp is one of a number of devices developed for this purpose. This description will assume use of a Mayfield clamp, but it is not specific to it].

A three-dimensional (3-D) digitiser, sometimes referred to as a pointer in this context, i.e. an instrument which can record the 3D position of its probe tip, is used to measure the position of uniquely identifiable patient features relative to some fixed co-ordinate system in the operating theatre.

The features of the patient, visible in the pre-operative imagery, corresponding to those whose position has been measured, as described above, are identified by manually marking their position on a computer display of the pre-operative data. The computer generating these displays has access to the output of the 3D digitiser and the pre-operative images and planning data.

Using the measurements of corresponding points, in the co-ordinate frame of the digitiser and in the co-ordinate frame of the pre-operative data, the co-ordinate transformation (between these two frames of co-ordinates) is calculated by a computer program.

With the transformation between digitiser co-ordinates and the pre-operative image co-ordinates known, the transformed position of the digitiser probe-tip, or a surgical instrument attached to the digitiser, can be plotted on computer displays of the pre-operative data or display, enabling the surgeon to locate his instruments to some pre-planned position or identify on the pre-operative data some visually observed feature, revealed during surgery.

The existing frameless stereotactic methods have disadvantages arising from restrictions due to nature of the 3D digitiser employed. A number of different techniques have been developed. [For references see A C F Colchester et al, "VISLAN: Combining Intra-Operative Video and Pre-Operative Images for Surgical Guidance" to be published in Proc. Applications of Computer Vision in Medical Image Processing Ed: G M Wells III, Menlo Park, AAAI Spring Symposium March 1994, AAAI Press]. A system, with a mechanical arm digitiser, is inherently difficult to manoeuvre and is time consuming to use if numerous features must be located to achieve registration; systems using acoustic or LED beacons require the hand-held pointer of the digitiser to have trailing wires or an internal power supply resulting in complexity in design and certification. Other disadvantages of the existing approaches are:

Loss of accuracy resulting from errors in the manual identification of patient features. (These can be reduced by the use of markers attached to the patient, if this is done before pre-operative imaging, but this carries risks of infection with markers held by screws into bone or errors due to skin movement if markers are attached to the skin by glue).

Loss of localisation capabilities, or errors, due to accidental or deliberate movement of the patient. The problem can be reduced by including a means of measuring the position of the clamp holding the patient, but this requires the patient to remain fixed in the clamp throughout surgery.

SUMMARY OF THE INVENTION

An aim of the present invention is to provide apparatus and a method of achieving localisation in frameless stereotaxy which does not suffer from the above mentioned problems.

According to the present invention there is provided apparatus for computer assisted surgery comprising camera means for viewing part of a patient's body, projector means for projecting a predetermined pattern of light onto the patient's body which is viewed by said camera means, processing and controlling means including image processing algorithms arranged to process said images from said camera means, and superimpose said images on images generated from data prestored in said controlling and processing means, display means for displaying said images and superimposed images, a passive pointer means having a predetermined pattern, which is viewed by said camera means and recognisable by said controlling and processing means, which is arranged to determine the position of a tip of said pointer means and orientation of said pointer means in relation to said patient's body and display said position on said display means with respect to said images generated from said data prestored in said controlling and processing means.

According to the present invention there is provided a method for use in computer aided surgery comprises the steps of:

generating at least one three dimensional image from a CT, MR or X-ray scan of part of a patient's body, projecting a predetermined pattern of light onto said part of said patient's body, viewing said pattern by camera means, generating a three dimensional image from said viewed pattern of light, combining said three dimensional images to give a common frame of reference, and, using a passive pointer means having a predetermined pattern enabling processing algorithms to determine the position of a tip of said passive pointer means and orientation of said pointer means in relation to the patient's body, and thereby identify the position of said pointer means in relation to the image generated from the CT, MR or X-ray scan.

BRIEF DESCRIPTION OF THE DRAWINGS

An embodiment of the present invention will now be described with reference to the accompanying drawings, wherein.

DESCRIPTION OF THE PREFERRED EMBODIMENT

Figure 1:
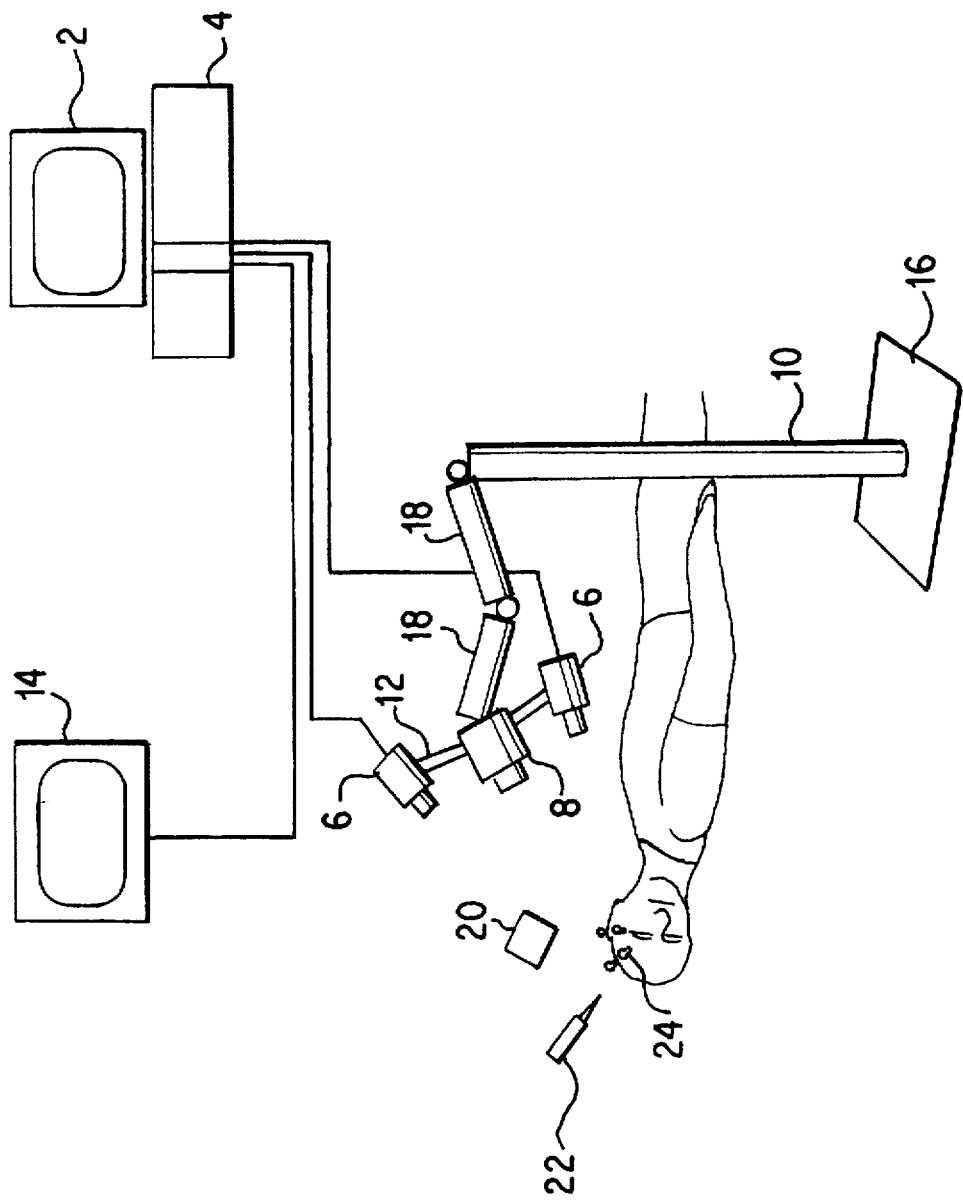
FIG. 1 shows a pictorial diagram of the apparatus required to perform the invention.

Referring to the drawings, the invention as described provides an alternative method of achieving localisation in frameless stereotaxy by using video cameras and a structured light projector to obtain intra-operative information about the position of patient features and of surgical instruments or pointers. The advantages of this method are that:

The video-based pointer can be freely hand-held without trailing wires or mechanical encumbrances.

The pointer does not contain active components, simplifying its design, certification, and sterilisation.

The position and shape of the surface feature, e.g. the patient's skin, can be measured very quickly using the cameras and projector without the laborious use of the 3D pointer.

The position of other features of the patient, such as blood vessels revealed during surgery, can be measured quickly with cameras alone, to provide a means of refining the transformation between the video camera system and the pre-operative images and plans.

The system does not require the use of special attachments to the patient during pre-operative imaging.

The errors or loss of capability due to accidental or deliberate movement of the patient can be detected and corrected by a number of methods, e.g. the use of markers attached intra-operatively to the patient, or supporting frame or operating table, at positions of convenience to the surgeon, or the use of patient positioning based on patient features such as revealed blood vessels.

As surgery progresses, the accuracy of registration to be refined is permitted using revealed patient features such as blood vessels.

Considering now the system components, and referring to FIG. 1, the system consists of the following main components.

Figure 2:
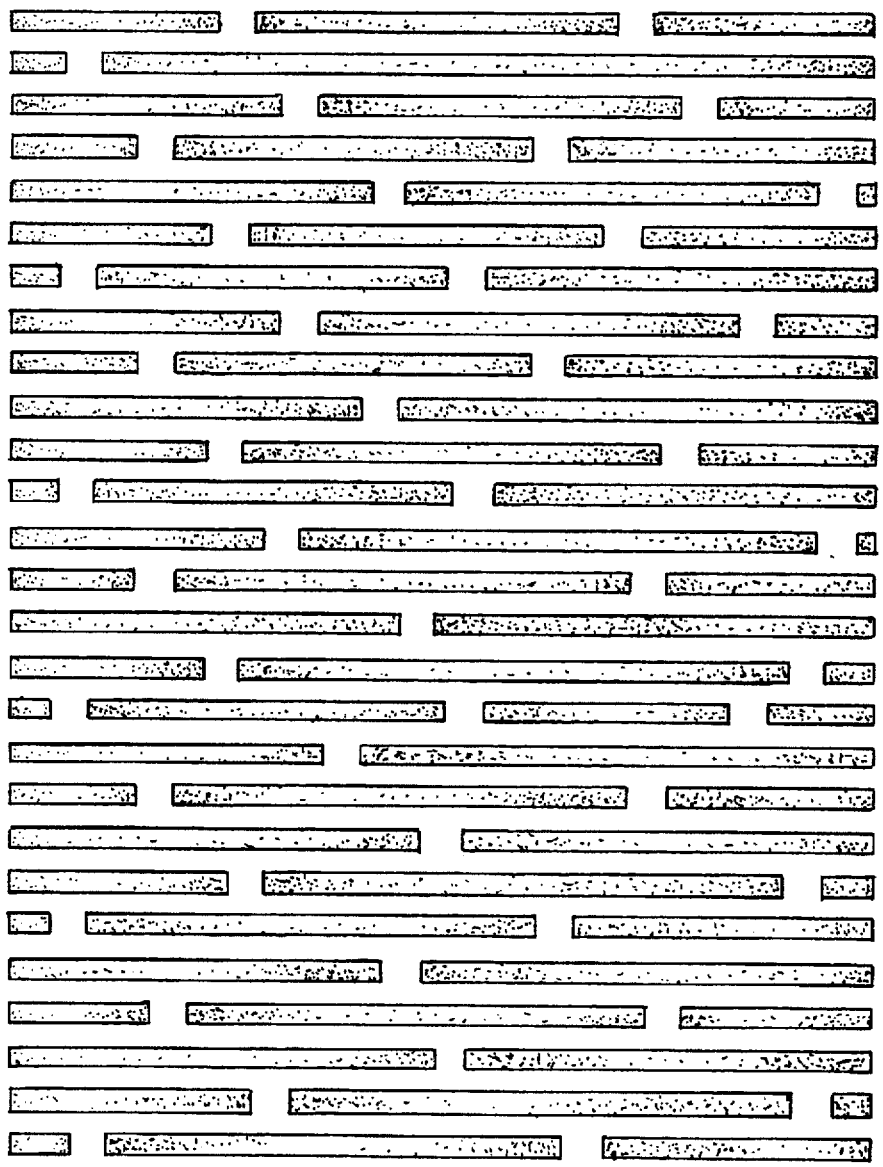
FIG. 2 shows the patterned slide used in the projector shown in FIG. 1.
Figure 3B:
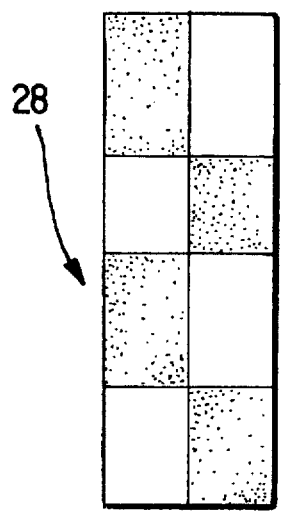
FIG. 3b shows an alternative linear acquisition target.
Figure 3A:
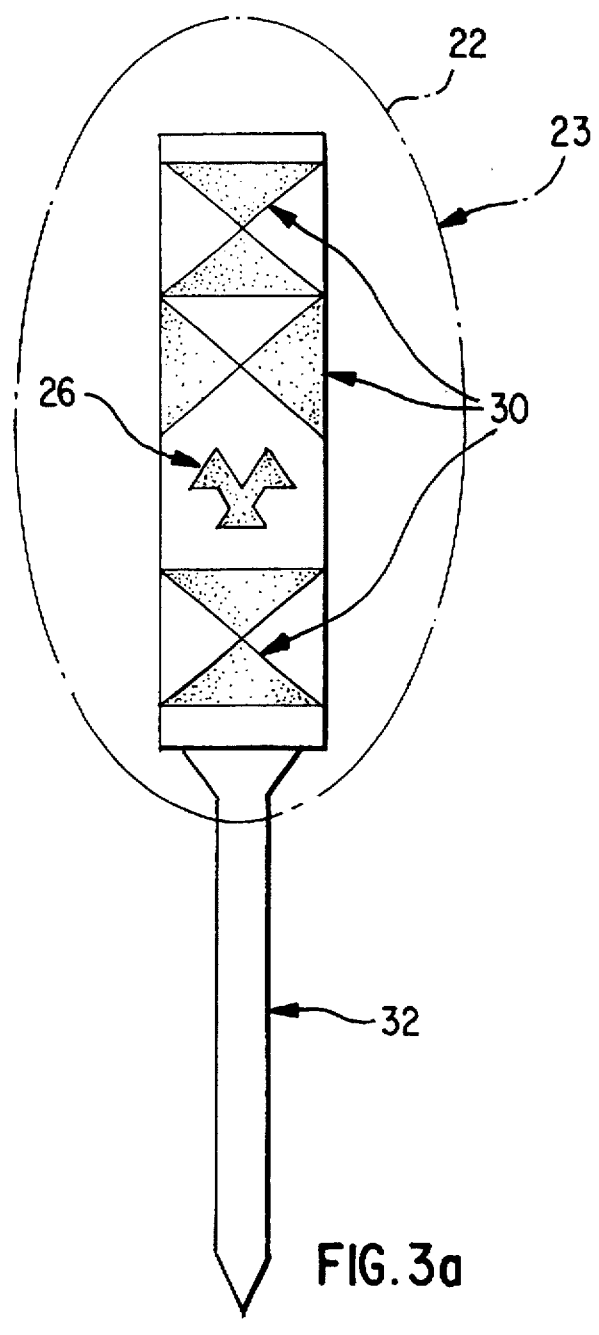
FIG. 3a shows a pointer handle and probe.

A workstation computer 2 with processor is provided having a display monitor and keyboard and/or mouse for normal computer interaction. An internal loudspeaker is also required for some system functions. Pre-operative data, images and surgical plans are loaded into this machine before surgery starts. A video frame grabber/video display card 4 is hosted by the workstation 2. At least one or more video cameras 6 are connected to the frame grabber. (In a different configuration, the cameras might be attached to, or use the optics of, the surgeon's operating microscope). A structured light projector 8 and slide is also provided. The projector is essentially a conventional slide projector, with appropriate lens to ensure the required field of projection and focus. The projected slide is as shown in FIG. 2. The breaks in the vertical bars are required to simplify processing algorithms. Different densities of bars may be used and different slides or more (or less) closely spaced bars and with different patterns or breaks may be used depending on the spatial resolution required. A stand 10 is provided for the cameras and projector. The stand is required to position the cameras and projector in a suitable position for viewing the relevant part of the patient. The stand consists of two main parts. Firstly, a base 16 and arms 18. The stand and arms are used to position the cameras 6 and projector 8 in the correct general viewing position. This is usually above the patient's chest or head for an operation on the head. In plan view, the surgeon, the surgical wound and the cameras should be placed in a straight line approximately. Secondly, a camera and projector mount 12. The mount 12 allows the position of the field of view of the cameras 6 and projector 8 to be adjusted from the general viewing position set by the placement of the stand and arms, using a pan-and-tilt device. The mount should allow a range of alternative spacings of cameras and projector and alternative vergeance angles so that the set-up can be adjusted for the particular operation in question. A video display monitor 14 is connected to the frame grabber and display card 4. A camera calibration tile 20 is provided for calibration purposes. The camera calibration tile is a flat plate with an accuracy measured array of dots on it. The calibration tile and its use are described by C G Harris and A Teeder "Geometric Camera Calibration for Vision-Based Navigation", Proceedings of IFAC International Workshop on Autonomous Vehicles, 18–21 Apr. 1993, Southampton UK, pp 77–82. A video pointer handle and probe 22 is a hand-held instrument. The hand-held component of the video-based pointer consists of a patterned handle 23 with a probe-tool attachment 32 such that the probe is rigidly fixed with respect to the handle in a known position when in use. Use of a bayonet fitting or similar fitting between handle and probe enables different tools to be attached to the handle (knives, suckers) for different purposes. The patterned handle is marked as shown in FIG. 3a. The handle has finger-grips positioned, either at the side of it or behind the patterned face-plate, so that the surgeon's fingers do not obscure the patterning when the pointer is in use, though the system can work with partial obscuration of the patterning. The patterning consists of two components. Firstly, a Binary Acquisition Target (BAT) 26. This is a symbol designed for quick detection and orientation by image processing algorithms. The shown symbol is one possibility, but there are others, e.g. the linear BAT 28 also shown in FIG. 3b. This linear target may also be used for tracking purposes. Secondly, a. Tracking Pattern 30. This is a set of marking designed to be suitable for video tracking purposes using the tracking algorithms, as described in GB Patent Application Number 9114518.5. The drawn pattern is one example as many variations of this are possible.

Figure 4:
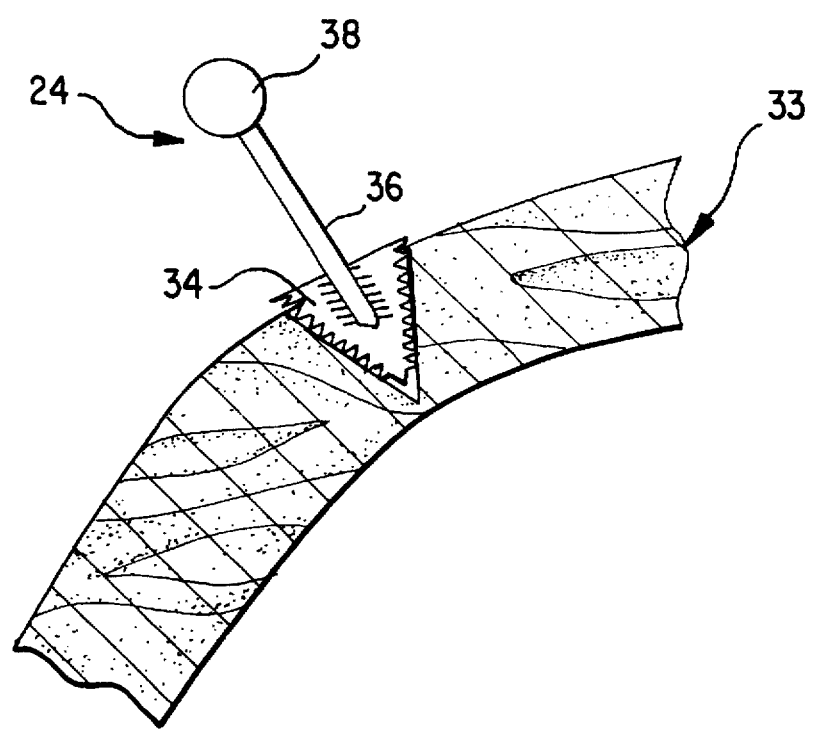
FIG. 4 shows an intra-operative marker pin connected to bone.

The Intra-Operative Markers (IOMs) 24, FIG. 1, may take several forms, though in all cases the markers need to be rigidly attached (directly or indirectly) to the patient when in use. Individual markers may be attached separately to the patient by screws which screw into the bone 33. These markers consists of three parts, a base section 34 which screws into the bone and a post 36 and a head 38, which screws into the base, as shown in FIG. 4. (The separable design allows the post and head to be removed temporarily and later replaced in the same position if it obstructs some part of the surgical procedure. Alternatively, a one-piece marker might be used where the surgical procedure allows). A minimum of three such markers are required. The head of the marker is finished in a bright matte finish to provide good visual contrast against its background. The shape of the marker-head is to enable it to be quickly and accurately located by image processing algorithms, thus a spherical head is very suitable, but other designs (e.g. ellipsoids, circular discs) might be used instead. For example, individual markers may be used which attach separately at convenient points to the Mayfield clamp, or similar clamp holding the patient, or to a separate dedicated clamp attached to the patient, or to the operating table. The heads of these markers are as described above. These markers may also be made in two parts for temporary removal, and may include a patterned block, containing a BAT and a tracking pattern similar to that used on the pointer handle. This is attached directly to the patient by a mechanism similar to a Mayfield clamp. As described above, part of the marker may be detachable for ease of use, and may include a patterned block as described above, but attached to the Mayfield clamp holding the patient, or to the operating table.

Considering now the system operation, the system is operated in the following stages which are described in the context of a surgical craniotomy.

The first step is camera set-up and calibration. With the patient lying on the operating table and clamped, if part of the surgical procedure, but not yet draped for surgery, the cameras 6 and projector 8 are positioned and adjusted to provide a suitable field of view. The calibration tile 20 is then held in the overlapping fields of view of the cameras and a set of pairs of images are captured, each pair of images consists of a simultaneously captured image from each camera.

The next step is the use of calibration algorithms, as described by Harris and Teeder above, running on the workstation 2, to calculate the relative position and orientation of the cameras 6 and parameters describing the imaging geometry of each camera (e.g. focal length, aspect ratio, image distortions). This process must be repeated if the cameras are moved relative to each other or if their imaging geometry is disturbed, but otherwise the cameras can be moved to a different view point or to view a different direction without repeating the calibration procedure.

The next step is the intra-operative skin surface measurement. Using the projector 8, the bar-patterned slide (FIG. 2) is projected onto the patient's skin and a pair of images is captured from the cameras. Using a processing algorithm running on the workstation 2, the shape and position of a section of skin surface illuminated by the projector is calculated relative to a particular camera. The processing will now be described.

A dense and accurate 3D representation of the (shaven) face or upper head is needed to permit matching to the surface extracted from MR or CT imagers. Accuracy's of better than 1 mm are believed required. Note that the upper head will consist of a single smooth, continuous surface.

Measurements of the surface will be performed using one or more cameras, for speed of acquisition and density of results. The surface is by itself devoid of prominent visual features, so visual features must be imposed on the surface. To obtain high accuracy (sub-pixel), support from a local region of the image is needed. One option for the surface features is a fine texture, but this has the disadvantages of variable accuracy, and the need to know the local surface slope (which will stretch the observed texture).

The preferred option is to use dark-light edges, imposed on the surface either by projection or 'painting'. These can be consistently located to high accuracy, and can be relatively dense. A Canny-type process is used, with a smoothing mask of size smooth (bold type is used to note algorithm parameters), and up to Nhysteresis steps of hysteresis to grow from the high threshold edgels into the low threshold edgels. The thresholds are obtained adaptively by taking the first moment of the distribution of edge strengths, the low threshold being a percentage of the high threshold. The density is limited by the size of the smoothing mask used in edge extraction—placing the edges closer together then this will cause the edges to be mis-positioned, as the support mask samples neighbouring edge strictures. Note that edges cannot be accurately located at junctions and sharp bends, and for this reason, a number, safety, of the first and last edgels of an edge are discarded. Edges shorter than min_length are discarded. Perhaps the strongest disadvantage of dark-light edges is the possibility of incorrect labelling of the edges—they have no distinguishing attributes excepting their polarity. This could be overcome by use of a chequerboard, but measurement accuracy will be lost near the junctions.

Three-dimension measurements of the location of surface features will be performed using stereo. One option is to use calibrated structured light, observed by a single camera, but this presents the problem of how to calibrate the structured light, and how stable is the calibration over time. The alternative selected is to use uncalibrated (but structured) surface edge features, observed by binocular (or trinocular) stereo cameras. Stereo calibration is essentially a solved problem, though there could be some difficulties with telephoto lenses. Using a conventional binocular stereo configuration, with the cameras spaced apart horizontally, the dark-light edges that give the greatest accuracy will be perpendicular to the epi-polar lines, thus they should be largely vertical in the images. Edges that are parallel with the epi-polar lines give no depth information, and this is another point against using a chequerboard.

Using stereo on dark-light edges requires the correct labelling of edges in each image, as there is no local test to check that the correct edges have been matched. The labelling problem is solved by firstly obtaining the correct relative labelling on each image individually, and then finding the difference in labelling between the two images.

To obtain the labelling on a single image, the adjacency between edges is first determined by sending out a set of 'feelers' on the image perpendicular to the edge, and noting which edges they first collide with. The feelers are sent out at an interval of poke_step between edgels along an edge, and have maximum length poke_length. The pair of edges with the greatest commonality are first labelled as 1 and 2. Next, the edge with the greatest commonality with the previously labelled edges is found, and appropriately labelled. This continues until no new edges are labelled.

The difference in labelling between the two images is currently determined by introducing randomly positioned breaks in the edges, which are seen as the start and end of edges. Each break should be able to be epi-polar matched between the images, though great accuracy is not expected, as it may be on a sharp curve. The epi-polar matching is deemed to be successful if it is within a distance of epi_polar_thresh pixels. This distinguishes between valid and invalid labelling differences. The labelling difference which is most popular is selected.

Once labelling has been achieved, each labelled pair of edges are considered separately. For each edgel in the prime camera (camera 0), the epi-polar line is constructed in the secondary camera image, and the pair of consecutive edgels in the secondary image that straddle the epi-polar line are found. By intersecting the epi-polar line and the line joining the straddling edgels, the intersection point is found. Now reciprocal depth varies linearly along the epi-polar line (in homogeneous co-ordinates). The start of the epi-polar line is location of the prime camera pin-hole, and the end of the epi-polar line has a reciprocal depth of zero. As before, a number, safety, of the first and last edgels of an edge are discarded because they may be inaccurate. To provide further security, the local orientation of both edges must be within an angle of epi_polar_angle degrees to the vertical.

The 3D edgels can be used to construct a triangular planar facet surface by use of Delaunay triangulation. Note every edgel is needed, since they are correlated, and edgels at an interval of delaunay_step are selected. Delaunay triangulation is performed in the prime image, and the resulting triangles interpreted as planar facets. This produces a single-valued surface. Any triangle with an edge exceeding max_triangle_size in length is discarded to stop the interpolation becoming too distant from the observations.

The next step is the registration of intra-operatively and pre-operatively measured skin surfaces. Using a processing algorithm, running on the workstation 2, the shape of the skin measured, as described above, is registered to the shape of the corresponding section of skin previously generated by analysis of pre-operative data. This results in the calculation of the co-ordinate transformation, T, between the pre-operative data and positions measured in theatre relative to the specified camera, as described above.

The processing algorithm to match the pre-operative and intra-operatively measured surfaces may be based on chamfer match procedures (D G L Hill and D J Hawkes, "Medical image registration using knowledge of adjacency of anatomical structures", Image and Vision Computing 12(3) 1994, in press). In this technique, a distance transform is calculated for the surface extracted from the pre-operative data, and is held as a set of voxels whose value represents the shortest distance to the pre-operative measurement of the scalp surface. A series of trial registrations are then attempted, by projecting points on the intra-operatively measured skin into the pre-operative co-ordinates. For each trial registration, the distance values of the voxels addressed by the projected points are summed to produce a cost of the trial. The final registration is taken as the minimum cost pose, found by using a genetic algorithm to refine an initial coarse estimate. Alternative methods are possible.

The next step is the marking of planned craniotomy position. With the patient and cameras remaining in the positions used, as described above, the surgeon is assisted in marking on the patient the planned site of craniotomy. This may be done in several ways. The live video output of a selected camera 6 is displayed to the surgeon with a graphical overlay generated by the frame grabber/video display 4. The overlay shows the outline of the planned craniotomy as if seen from the position of the selected camera. The position of this overlay can be calculated in the workstation, from its planned position relative to the pre-operative data and the transformation, T. The surgeon now marks the skin surface manually, in the normal way, but he looks at the video display to ensure that the marker pen and plan are in alignment. The marker pen used by the surgeon is fitted to the patterned handle of the video pointer 22. Using the video pointer 22, the position of the marker-tip is now tracked relative to the camera 6, and, by means of the transformation, T, its position relative to pre-operative images and plans can be calculated. The surgeon may now mark the planned craniotomy on the patient, by observing the position of the pen-tip on a display of pre-operative data or by listening to a audio signal indicating the proximity of the pen-tip to the planned position.

The next step is the placement and modelling of intra-operative markers 24. Having marked the craniotomy position on the patient, the surgeon now places IOMs 24 at positions of convenience (but within the field of view of the cameras 6), either attaching a patterned block or individual markers to the Mayfield clamp, or operating table or directly to the patient, depending on the type of IOM in use.

The position of the markers 24 and position and shape of the skin surface is now measured, relative to the camera system. The skin surface is measured, as described above. (This step can be omitted if the position of the cameras and patient has remained unchanged since that step was performed). A pair of images is also captured, without the patterned illumination from the projector 8. These images are processed in the workstation to determine the layout and position of marker pin heads (if separate markers were used) or to determine the position of the IOM block (if a block were used). With independent markers, the position of each marker head is calculated relative to the camera system. The processing algorithms will now be described.

The pin tracking module is designed to find movement of the patient relative to the camera 6. The program works in two modes, 'create' and 'find'. In create mode, the individual marker pin positions are measured and stored in a file as the model with which pin positions are compared after patient-camera movement. After movement, find mode is operated, in which the new 3D pin positions are measured, and the old and new positions compared to calculate the relative movement.

Create Mode

The steps in create mode are:

Two images are captured and stored in arrays.

Circles are found in each image as follows. A local mean removal (LMR) algorithm is applied which subtracts off the local background intensity, so removing noise and enhancing edges. The LMR code then assigns a class number to each pixel, by comparing it with pre-set thresholds. This 'class' image is then stored as the working image. For each working image, a connected component finder algorithm is applied, which searches for groups of connected pixels of the same class, and labels each group as an object. It also finds the outline pixels for each object. Each object is examined to see if it satisfies the criteria for being a candidate to be a circle, i.e. width, height, and class are checked. Candidate circles are checked by the circle-finding routine, which fits a circle to the object outline, using a general least squares minimisation routine, and returns its radius, centre and error in fit. Those with acceptable errors are stored as a list of circles. Matching circles in the two images are identified using epi-polar matching, and their 3D positions calculated, using the known camera position. The 3D positions are stored as the pin model.

Find Mode

Steps 1–3 in 'find mode' are identical to those described above. The 3D positions of the pins are stored in an array to form the object to which the pin model is to be matched. The pin model is read in and the two sets of pin positions passed to a closed-form least-squares minimisation algorithm which finds the best-fit motion of the model about the camera position to bring it onto the object position. It is necessary to tell the algorithm which model pin matches which object pin before the fit is performed. In practice, as the pins are placed in a circle, it is easy to order them according to angle about their centroid giving N possible match arrangements for N pins.

With an IOM block, whose shape and patterning is already known, the tracking algorithms may be used to determine its position as hereinater described.

The intra-operative and pre-operative measurement of the skin surface are now registered again, as described above, and the resulting updated transformation, T, is used to calculate the position of the markers relative to the pre-operative images and plans. This information is stored for future use following relative movement of camera and patient.

At this point surgery now commences, and at various times the surgeon may wish to use the video-based pointer 22 (or its handle with another instrument attached) to help relate some intra-operative position to the pre-operative data. This may be done by real-time processing of images in two phases as follows:

Acquisition—The surgeon holds the pointer 22 still, with its patterning facing the cameras. Processing algorithms locate the BAT in corresponding images from each camera and an approximate estimate of the position of the BAT, relative to the cameras is calculated. This position is used as an initial estimate for the tracking phase. Successful completion of this phase is indicated by an audible signal and the surgeon may start to move the pointer. The processing algorithm for BAT acquisition will now be described.

Image processing algorithms for locating the binary acquisition target, shown in FIG. 3a, proceed in a series of steps.

The first steps segment potential BAT objects from the field of view, as follows:

1) The input grey-level image is processed by local mean removal and thresholding to produce a binary output image.

2) Connected (black-pixel) components are then found. The following steps identify the BAT from the set of connected components.

3) The set of components arising from step 2 are filtered according to component size to remove very small items resulting from image noise and clutter.

4) The convex hull of each remaining connected component is calculated.

5) Significant concavities in object boundaries are found by comparing the true boundary with the convex hull, and objects with other than three major concavities are rejected.

6) Again by comparing the true boundary with the object's convex hull, the six points marking the end of each concavity are found.

7) The distances between opposite pairs of points from step 6 are compared. In orthographic projection, these distances would be equal for the true BAT, because the expected convex hull is hexagonal, consequently objects with significantly unequal opposite distances can be rejected. In practice the comparison of distances allows for the fact that the viewing geometry has perspective and is not simply orthographic. The remaining steps calculate the pose of the BAT.

8) The position and orientation of the BAT, relative to the camera, is now calculated from the image positions of the six points defining the near-hexagonal convex hull, ignoring the rotational ambiguity, using knowledge of the actual dimensions of the BAT and the camera calibration parameters.

9) With three possibilities for the pose of the BAT calculated in step 8, differing only by 120 degree rotations of the BAT, the rotational ambiguity is now resolved by calculating the position of three test pixels, to locate the deepest cut in the BAT's hexagonal convex hull.

This process can be repeated for images from each of the cameras and the resulting set of pose estimates can be integrated for improved accuracy.

Tracking—Using the BAT position estimate calculated at acquisition, the tracking pattern is tracked using the tracking algorithms as described in GB Patent Application Number 9114518.5. The accuracy of this phase is improved by an extension of the tracking algorithms to use information from two or more cameras 6. Using the transformation, T, the position of the pointer 22 or tool-tip can be superimposed on displays of pre-operative images or plans. As the tracking algorithms track its target in orientation as well as position, the orientation of the pointer can be displayed. Should the system fail to track the pointer, this can be detected by the system and an audible warning generated.

Registration of intra-operatively and pre-operatively measured patient features revealed in surgery. In the course of surgery, other patient features will be revealed to the intra-operative cameras. A particular example is the network of pial blood vessels revealed after removal of the dural membrane. Depending on the intra-cranial pressure, tissue may rise or fall on opening the craniotomy, and tissue may be misplaced relative to its pre-operative position. The intra-operative position and shape of these blood vessels can be measured by processing a new pair of images and the feature registered to pre-operative measurements. This registration provides a second estimate of that transformation, T. This second estimate may be used to replace or refine the original estimate of T. Similar techniques may be applied to other patient features.

Considering now the re-location of the patient following movement of patient or cameras. From time to time, it may be necessary to move the cameras or the patient, for the convenience of the surgeon to improve surgical access or line of sight, or movement may occur for some accidental reason. Following such movement, the transformation, T, must be re-calculated. If the skin surface is no longer visible, for example, because of surgical wadding and drapes, this may be done by capturing a new pair of images containing the IOMs 24 (without projector illumination). Where the IOMs 24 consists of a patterned block, its new intra-operative position may be measured, as described above, and T can be updated because the IOM's position relative to pre-operative data has been calculated, as described above. Where individual markers are used, the newly captured pair of images is used to make a second measurement of the marker head positions and a further registration algorithm estimates the best common transformation, T, between original and current IOM positions. The processing algorithms for this operation have been described above with respect to the placement of the IOM's. The transformation, T, between the camera system and pre-operative images and plans can now be revised.

The sources of movement which can be accommodated, depend on the type and fixing of IOM used. All the types described above can be used to accommodate deliberate movement of the operating table or camera and projector mount. If movement occurs accidentally because the head slips in the Mayfield support clamp, then recovery from this situation requires the IOMs to have been fixed directly to patient.

Intra-operative visualisation of pre-operative plans may be required by the surgeon at various stages in surgery. This may be done, as previously described, by overlaying transformed planning data on live video from a selected camera.

It will be appreciated that various modifications may be made to the foregoing described procedure and apparatus, are possible which fall within the scope of the invention. For example, any number of cameras may be used, and variations to the algorithms used may be envisaged.

We claim:

1. An apparatus for computer assisted surgery comprising:

camera means for viewing a part of a patient's body, projector means for projecting a predetermined bar pattern of light onto the part of the patient's body being viewed by said camera means, processing and controlling means connected to said camera means for generating three-dimensional intra-operative images of the part of the patient's body from signals generated by the camera means representative of a view of said predetermined bar pattern projected onto the part of the patient's body, said processing and controlling means operating to combine said three-dimensional intra-operative images with pre-operative three-dimensional images generated by a scanner and pre-stored in said processing and controlling means into a combined image, and display means, coupled to said processing and controlling means, for displaying said combined image, wherein said processing and controlling means operates to combine the intra-operative and pre-operative images in accordance with the following steps:

(i) defining, with respect to a scanner based co-ordinate system and from analysis of said pre-operative images, a representation of measured shape and position of the part of the patient's body, (ii) identifying features of interest in said pre-operative images with reference to the scanner based co-ordinate system, (iii) defining, with respect to an intra-operative camera based co-ordinate system and from analysis of said intra-operative images in dependence upon said predetermined bar pattern, a further representation of measured shape and position of the part of the patient's body, (iv) calculating a co-ordinate transformation between said intra-operative camera based co-ordinate system and said scanner based co-ordinate system by matching said pre-operative and intra-operative images, (v) calculating positions of said features of interest with respect to said intra-operative camera based co-ordinate system depending upon said co-ordinate transformation and said features of interest, and (vi) combining said pre-operative and intra-operative images to provide localization for frameless stereotaxy without performing manual registration of features of the patient.

2. An apparatus as claimed in claim 1, and further including a passive pointer having a predetermined acquisition pattern attached thereto, which passive pointer is viewed by said camera means, wherein the processing and controlling means operates to recognize a position and an orientation of the pointer relative to said intra-operative camera based co-ordinate system from said acquisition pattern, to calculate the position of said passive pointer within said scanner based co-ordinate system in accordance with said co-ordinate transformation, and to superimpose, on said combined image, the position and the orientation of the passive pointer.

3. An apparatus as claimed in claim 2, wherein the processing and controlling means further operates to track movement of the pointer with respect to said intra-operative camera based co-ordinate system as the pointer correspondingly moves within a field of view of the camera means, and to accordingly display movement of the pointer in said combined image.

4. An apparatus as claimed in claim 2, wherein the predetermined acquisition pattern has a binary acquisition target, said passive pointer includes a handle extending from said pointer, and said binary acquisition target is disposed on said handle to facilitate recognition of said passive pointer by the processing and controlling means.

5. An apparatus as claimed in claim 2, wherein said camera means comprises at least two video cameras to provide intra-operative measurement data which are representative of a three-dimensional image.

6. An apparatus as claimed in claim 5, and further comprising calibration means for calibrating the intra-operative measurement data provided by said at least two video cameras.

7. An apparatus as claimed in claim 1, wherein calculating said co-ordinate transformation includes using an algorithm.

8. An apparatus as claimed in claim 1, wherein said projector means is a slide projector provided with a slide, said slide comprising a pattern of broken bars to generate the predetermined bar pattern.

9. An apparatus as claimed in claim 1, wherein the pre-operative images are formed from any of X-ray images, MR scan images and CT scan images.

10. An apparatus as claimed in claim 1, wherein intra-operative markers are attached to the part of the patient's body and used by said processing and controlling means to compensate for movement by the patient.

11. An apparatus as claimed in claim 10, wherein each of the intra-operative markers comprises a base section for screwing into a bone of the patient, a post secured to said base section and a head attached to said post and opposite to said base section, said head being easily recognized by said processing and controlling means.

12. An apparatus as claimed in claim 11, wherein said head includes a pattern which is viewed by the camera means and the processing and controlling means recognizes said pattern for determination of a position of the head with respect to the combined image.

13. A method for use in computer aided surgery comprising the steps of:

using a scanner to generate pre-operative three-dimensional images relating to a part of a patient's body, projecting a predetermined bar pattern of light onto the part of the patient's body, viewing said predetermined bar pattern, generating intra-operative three-dimensional images in accordance with captured intra-operative images and the predetermined bar pattern projected on the part of the patient's body, defining, with respect to a scanner based co-ordinate system and from analysis of said pre-operative images, a representation of measured shape and position of the part of the patient's body, identifying features of interest in said pre-operative images with reference to the scanner based co-ordinate system, defining, with respect to an intra-operative camera based co-ordinate system and from analysis of said intra-operative images in dependence upon said predetermined bar pattern, a further representation of measured shape and position of the part of the patient's body, calculating a co-ordinate transformation between said intra-operative camera based co-ordinate system and said scanner based co-ordinate system by matching said pre-operative and intra-operative images, calculating positions of said features of interest with respect to said intra-operative camera based co-ordinate system depending upon said co-ordinate transformation in combination with positions of said features of interest, combining said pre-operative and intra-operative images into a combined image to provide localization for frameless stereotaxy without a requirement for performing manual registration of the part of the patient's body, and displaying said combined image.

14. A method as claimed in claim 13, and further comprising the steps of:

providing at least two cameras, disposing a calibration tile in view of said at least two cameras, calibrating said cameras in accordance with captured images so that each camera captures the same image for viewing said predetermined bar pattern depending upon a view of said calibration tile, and calculating a relative position and orientation of said at least two cameras.

15. A method as claimed in claim 13, and further comprising the steps of:

using a passive pointer having a predetermined acquisition pattern, determining a position of said pointer with respect to said intra-operative camera based co-ordinate system from said acquisition pattern, calculating the position of said pointer within said scanner based co-ordinate system, and creating the combined image and showing the position and orientation of the passive pointer.

16. A method as claimed in claim 15, and further comprising the steps of tracking movement of the pointer with respect to said intra-operative camera based co-ordinate system as the pointer correspondingly moves, and displaying said movement in said combined image.

17. A method as claimed in claim 13, and further comprising the steps of positioning intra-operative markers on the patient's body, measuring movement of the part of the patient's body in accordance with relative movement of the intra-operative markers, and compensating for the movement of the part of the patient's body by correspondingly adapting said combined image in accordance with said movement.

* * * * *